(12) United States Patent
Buchwald et al.

(10) Patent No.: US 9,689,809 B2
(45) Date of Patent: Jun. 27, 2017

(54) CONTAINER HANDLING DEVICE FOR HANDLING CONTAINERS, SUCH AS BOTTLES OR SIMILAR CONTAINERS DESIGNED TO HOLD A BEVERAGE OR A SIMILAR PRODUCT

(71) Applicants: Carsten Buchwald, Sinzig (DE); Wolfgang Schorn, Hönningen (DE)

(72) Inventors: Carsten Buchwald, Sinzig (DE); Wolfgang Schorn, Hönningen (DE)

(73) Assignee: KHS GmbH, Dortmund (DE)

( * ) Notice: Subject to any disclaimer, the term of this patent is extended or adjusted under 35 U.S.C. 154(b) by 89 days.

(21) Appl. No.: 14/837,068

(22) Filed: Aug. 27, 2015

(65) Prior Publication Data

US 2015/0369754 A1    Dec. 24, 2015

Related U.S. Application Data

(63) Continuation-in-part of application No. PCT/EP2014/000090, filed on Jan. 15, 2014.

(30) Foreign Application Priority Data

Feb. 28, 2013   (DE) .................. 10 2013 101 995

(51) Int. Cl.
*G01N 21/90* (2006.01)
*G01M 11/04* (2006.01)
(Continued)

(52) U.S. Cl.
CPC .............. *G01N 21/90* (2013.01); *B65B 3/04* (2013.01); *B65B 43/50* (2013.01); *B65B 55/24* (2013.01);
(Continued)

(58) Field of Classification Search
CPC .. A61L 2/235; B67C 3/12; B65B 3/04; B65B 43/50; G01N 21/90
(Continued)

(56) References Cited

U.S. PATENT DOCUMENTS 2,593,311 A * 4/1952 Johnson .................... B08B 9/42
134/127
3,674,198 A * 7/1972 Eberle ....................... B04B 5/04
211/74

(Continued)

FOREIGN PATENT DOCUMENTS

DE      3611536 A1    10/1987
DE  102006034432 A1    1/2008
(Continued)

OTHER PUBLICATIONS

German Office Action 10 2013 101 995.1 dated Nov. 6, 2013.
International Search Report PCT/EP2014/000090 dated Jun. 16, 2014.

*Primary Examiner* — Tri Ton
*Assistant Examiner* — Jarreas C Underwood
(74) *Attorney, Agent, or Firm* — Nils H. Ljungman & Associates

(57) ABSTRACT

A container inspection device is used to inspect containers, such as bottles or similar containers in a container filling plant. The container inspection device comprises a guide arrangement that guides characteristic information of one or more regions of a container along a first guide path to a first sensor, and along a separate, second guide path to a second sensor. The guide arrangement comprises at least two essentially identical guide structures, through which the guide paths travel. A guide element is included that is designed to guide the characteristic information to both the first guide path and the second guide path.

20 Claims, 11 Drawing Sheets

(51) Int. Cl.
- *G02B 7/00* (2006.01)
- *G02B 23/04* (2006.01)
- *B65B 3/04* (2006.01)
- *B65B 43/50* (2006.01)
- *B65B 55/24* (2006.01)

(52) U.S. Cl.
CPC .......... *G01M 11/04* (2013.01); *G01N 21/9009* (2013.01); *G02B 7/003* (2013.01); *G02B 23/04* (2013.01)

(58) Field of Classification Search
USPC ............... 356/239.1–239.5, 237.1–237.6, 356/242.1–243.8, 426–431, 600–640; 53/471–473, 448–452, 558
See application file for complete search history.

(56) References Cited

U.S. PATENT DOCUMENTS

| | | | | |
|---|---|---|---|---|
| 4,122,937 A | * | 10/1978 | Vischer | B08B 9/42 198/408 |
| 4,551,627 A | * | 11/1985 | Reich | B07C 5/3408 250/223 B |
| 4,636,635 A | * | 1/1987 | Kronseder | G01N 21/9009 209/526 |
| 5,441,063 A | * | 8/1995 | Fernandez | B08B 9/32 134/142 |
| 5,490,011 A | | 2/1996 | Pernick et al. | |
| 5,659,652 A | * | 8/1997 | D'Entremont | B23Q 1/015 248/73 |
| 6,034,821 A | * | 3/2000 | Schenfeld | G02B 6/4249 359/618 |
| 6,172,748 B1 | * | 1/2001 | Sones | G01N 21/9054 356/237.1 |
| 6,937,339 B2 | * | 8/2005 | Yamazaki | G01N 21/9027 356/239.6 |
| 7,428,110 B2 | * | 9/2008 | Tamada | G02B 7/003 353/101 |
| 7,488,965 B2 | * | 2/2009 | Cochran | G01N 21/8806 250/223 |
| 9,057,707 B2 | * | 6/2015 | Buchwald | G01B 11/25 |
| 9,108,835 B2 | * | 8/2015 | Hayakawa | B67C 3/242 |
| 2004/0264841 A1 | * | 12/2004 | Utkin | G02B 7/1805 385/16 |
| 2006/0292038 A1 | * | 12/2006 | Johansson | G01N 35/025 422/82.05 |

FOREIGN PATENT DOCUMENTS

| | | |
|---|---|---|
| DE | 10 2008 029 661 A1 | 12/2009 |
| GB | 2373556 A | 9/2002 |

* cited by examiner

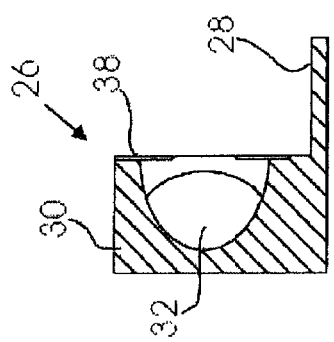
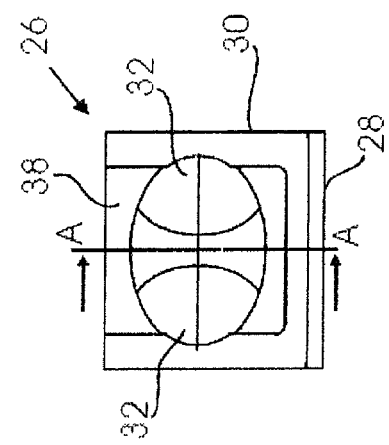

CONTAINER HANDLING DEVICE FOR HANDLING CONTAINERS, SUCH AS BOTTLES OR SIMILAR CONTAINERS DESIGNED TO HOLD A BEVERAGE OR A SIMILAR PRODUCT

CONTINUING APPLICATION DATA

This application is a Continuation-In-Part application of International Patent Application No. PCT/EP2014/000090, filed on Jan. 15, 2014, which claims priority from Federal Republic of Germany Patent Application No. 10 2013 101 995, filed on Feb. 28, 2013. International Patent Application No. PCT/EP2014/000090 was pending as of the filing date of this application. The United States was an elected state in International Patent Application No. PCT/EP2014/000090.

BACKGROUND

1. Technical Field

The present application relates to a container handling device for handling containers, such as bottles or similar containers designed to hold a beverage or a similar product.

2. Background Information

Background information is for informational purposes only and does not necessarily admit that subsequently mentioned information and publications are prior art.

The present application concerns a container handling device for handling containers, such as bottles or similar containers designed to hold a beverage or a similar product. This application also relates to a container handling device that includes an inspection device for inspecting containers, for example bottles. Moreover, the inspection of at least one region of the container takes place optically by cameras or other devices for obtaining images or image information.

In some beverage bottle or beverage container inspection systems, empty bottles or similar containers are moved past an inspection device, wherein, for example, an optical inspection takes place from above, while a lighting device is arranged underneath or adjacent an area to be illuminated for inspection. Various regions of a bottle or of any other container can be checked, for example the bottle base or bottom, or the bottle mouth or neck area. To this end, taking photographs or other images of the regions of the containers with multiple cameras can be performed.

Some inspection devices for inspecting bottles or similar containers can be designed to inspect the inside of a bottle after cleaning for undesirable objects, contaminants, dirt and/or damage, such as scratches or chips or other such flaws or damage. In one example, five cameras are arranged on one optical channel. Inside the optical channel, optical elements such as beam splitters or lenses are provided so that each camera can observe the allocated region. Consecutive beam splitters thereby provide different penetration and reflection values in each case. Beam splitters or beam-splitting optical elements, as described herein and in accordance with one possible embodiment, are partially transparent optical elements that reflect part of the light incident thereon, and that transmit part of the light incident thereon. These types of optical elements can have different transparency values and reflection values.

OBJECT OR OBJECTS

It is the object of the present application to describe a container handling device for handling containers, such as bottles or similar containers designed to hold a beverage or a similar product, which container handling device includes an inspection device that can be used in a variable manner in the container handling device.

SUMMARY

The object may be accomplished in a container handling device for handling containers, such as bottles or similar containers designed to hold a beverage or a similar product, which container handling device, according to at least one possible embodiment, includes an inspection device and a channel element for the inspection device. Other possible embodiments of the present application are disclosed herein.

A starting point of the present application is the consideration that changes in the structure of the inspection device are to be simplified, so that the inspection device can be easily adapted for different application purposes, for example for different types of containers or containers having different shapes or dimensions, in which the regions are to be checked with a different number of cameras.

The inspection device according to the present application has an optical channel on which at least two cameras can be arranged. Thereby, optical paths run through the optical channel in each case between the cameras and the container. By using a beam-splitting element, a first optical path can be divided into two to provide a second optical path, so that two different cameras can inspect the container, in one possible embodiment a beverage bottle, via the optical channel.

According to the present application, it is provided that the optical channel, that is, the structure through which the optical paths run, has at least two identical channel elements. As explained in more detail in the possible embodiments disclosed herein, the optical channel can be built in a modular manner from a plurality of such identical channel elements, which are secured next to each other. The channel elements moreover each have openings through which the optical paths may run.

By using at least two, but in one possible embodiment other additional, identical channel elements, the optical channel can be made in a modular fashion. In this way, it is possible to assemble adapted optical channels from the channel elements for various applications, wherein by the use of a multiplicity of identical elements, some benefits in the form of savings arise. An existing system can easily be converted by a modified arrangement of the channel elements. In other words, by using individual, identical channel elements in a modular fashion, the inspection unit can be modified or customized by using different numbers of the channel elements or channel modules to achieve a different inspection function, depending on the type of container to be inspected, the specific type of inspection to be performed, or the spatial requirements of the machine in which the inspection unit is to be installed. For the manufacturer of such inspection units, manufacturing costs can be reduced by making identical channel elements that can be assembled as desired to produce a desired configuration. Whether the manufacturer is manufacturing an inspection unit to be retrofitted on an existing machine of a customer, or inspection units to be used in the manufacturer's own container handling machines, different configurations can be easily achieved. Alternatively, the manufacturer could provide a plurality of the identical components, such as the channel elements and cameras, to a customer as part of an inspection unit kit or installation pack. The manufacturer could then assemble the inspection unit based on the spatial requirements of the container handling machine and the desired inspection function. The manufacturer therefore avoids the expense of creating individual, customized inspection units for each customer. Further, if the customer finds that the initial configuration of the inspection unit is not optimal, the customer can easily modify the configuration since the components are identical and can be easily changed to a different orientation with respect to one another.

According to a further development of the present application, the channel elements are each designed as hollow elements in which a wall or frame encloses an interior space. The openings for the optical paths are thereby provided in the wall or the walls of the frame. The interior space can be used to hold optical elements, such as, for example, mirror elements, lenses, colored filters or beam splitters. The wall or walls can be made for example of metal, e.g. aluminum or a special steel. The wall areas are made in one piece or connected undetachably to each other so that a desired high level of stability and essentially exact or general orientation are essentially guaranteed or promoted. In at least one possible embodiment, the hollow elements can be closed at least on one side, or, in another possible embodiment, on two opposite sides, by demountable or removable cover plates. In this way, optical elements introduced into the channel elements can be positioned and, in one possible embodiment, also secured by connecting to at least one of the cover plates.

In a possible embodiment, the channel elements are in each case designed as a rectangular shape, or possibly a cubic shape, and the openings for the optical paths are arranged in the lateral or side areas. In this way, an optical channel can be built in a modular manner, in which the optical paths run in each case parallel or substantially parallel or at right angles. In one possible embodiment, a rotationally symmetrical structure of the rectangular channel elements, and in one possible embodiment a cube shape, are possible.

Due to the rotationally symmetrical structure of the channel elements, the channel elements can be used in various structures in a very variable manner, wherein the optical paths in different directions are always or substantially always of the same lengths. This possibility is evident in cube-shaped channel elements where the length of the optical paths is in one possible embodiment a whole-number multiple of the length of a side of the cubes. The remaining optical structure, for example lens systems, can be adapted to the corresponding beam paths.

According to a possible further development of the present application, the channel elements each have at least three openings, through which an optical path can run. Moreover, it is further possible that a first and second opening are arranged in alignment with one another, with a third opening at an angle to them, in one possible embodiment at a right angle. A bracket for an optical element, such as a beam-splitting element or a mirror element, can be provided so that an optical path runs from the first opening through a reflection on the beam-splitting element/mirror element to the third opening. In the event of the beam-splitting element, the beam is split into two, so that one portion of the beam follows the first optical path, and a second portion of the beam follows a second optical path that runs from the first opening to the second opening arranged in alignment with the first opening.

For the arrangement of optical elements, such as, for example, beam-splitting elements, mirror elements, optical filters or lens elements on the channel elements, a fixed bracket or holder, for example, can be provided there. According to a further development of the present application, alternatively an insert for the channel elements is provided as such a holder or bracket. In this way too, the modular structure of an optical channel is supported or promoted or maintained.

An insert of this kind, in one possible embodiment, can be inserted in a channel element such that the operation or structure or function of the channel element can be changed. For example, a rectangular or cubic channel element can have in each case centrally arranged openings in at least four lateral or side areas for the optical paths, while it can have an opening for introducing the insert as a bracket for optical elements on one or two lateral or side areas. In one possible embodiment, it is possible to push an insert into a channel element and thereby to guide the insert already on the channel element and thus to position it accordingly precisely or desirably. The openings in the lateral areas can be closed by cover plates on which, in one possible embodiment, the insert can also be secured.

According to one possible embodiment, an insert as a bracket for an optical element, for example a beam-splitting element, mirror element, optical filter element or lens element, has at least one opening for the optical path to pass through. In a possible embodiment, two openings are provided on one insert, said openings forming an angle, in one possible embodiment a right angle, to each other. An insert can be fitted with a triangular holding body so that a mirror or beam-splitting element is arranged at an angle to an incoming optical path, in one possible embodiment at less than forty-give degrees. In alternative embodiments, a holding body can also have a different cross-sectional shape, for example a trapezoidal shape, so that an optical path can be split twice or multiple times.

In each case, lateral areas with a number of mounting holes can be provided on channel elements. In this way, to form the optical channel, it is possible, for example, to connect the channel elements directly to each other or to further brackets, such as by using screws or bolts. The cameras can also be secured on the optical channel in the same way. In this regard, it is possible that, on the channel elements, an arrangement of such mounting holes, such as a so-called drill pattern, is provided, which is in each case identical. In this way, a possibly fitting arrangement is automatically essentially ensured or promoted where mounting holes are used.

To depict the region observed in each case on the camera, different optical elements can be provided. In one possible embodiment, a lens element can be arranged between the optical channel and the container. In one possible embodiment, a lens system with multiple lens elements is provided there.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

FIG. 2 shows, in a side view, an insert for the optical channel from FIG. 1;

FIG. 2A shows a view of the section along the line A-A in FIG. 2;

DESCRIPTION OF EMBODIMENT OR EMBODIMENTS

Figure 1:
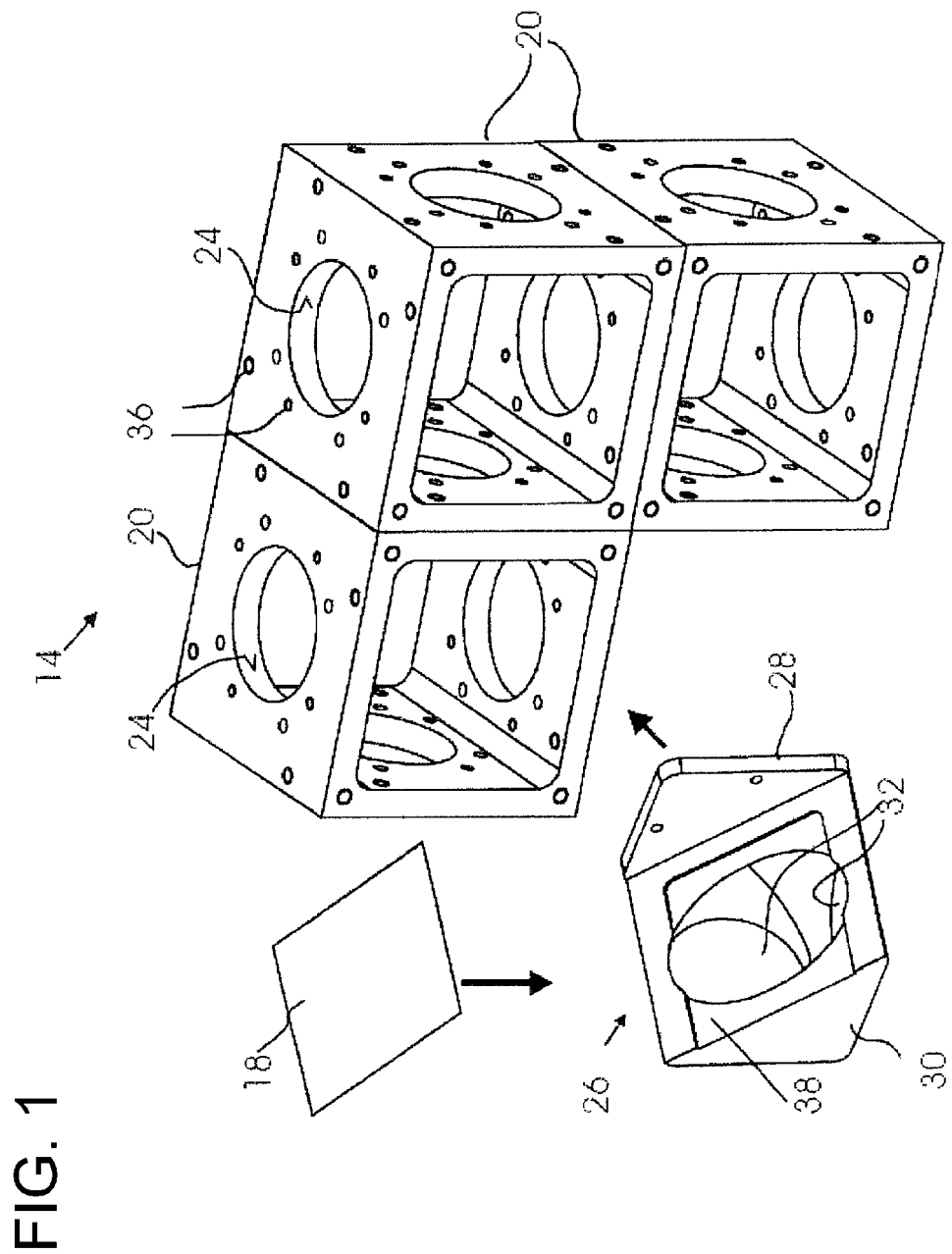
FIG. 1 shows, in a perspective exploded view, elements of an optical channel.
Figure 1A:
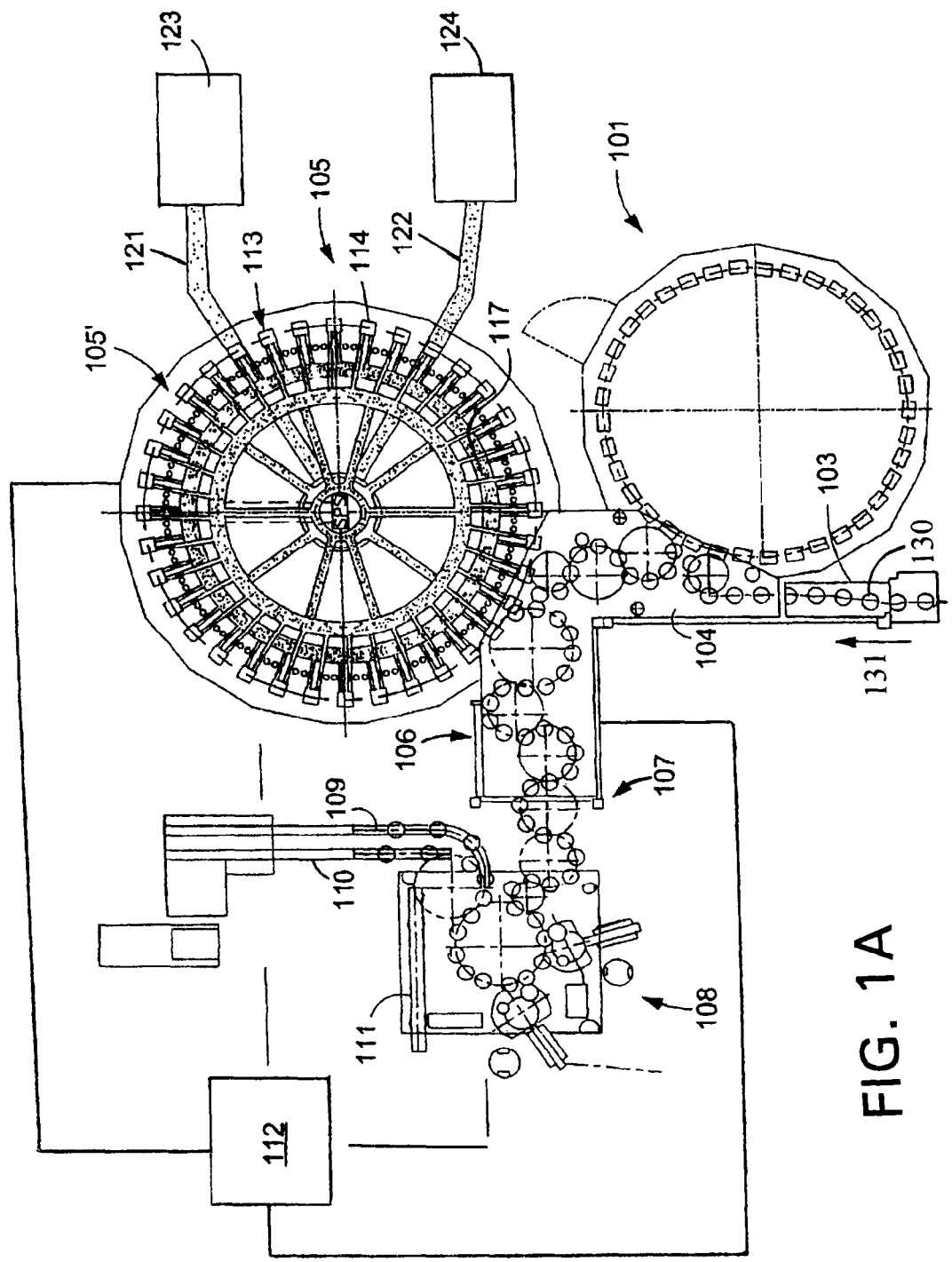
FIG. 1A shows schematically the main components of an example of a system for filling containers, specifically, a beverage bottling plant for filling bottles with at least one liquid beverage.

FIG. 1A shows schematically the main components of an example of a system for filling containers, specifically, a beverage bottling plant for filling bottles 130 with at least one liquid beverage, in which system or plant could possibly be utilized at least one aspect, or several aspects, of the embodiments disclosed herein.

FIG. 1A shows a rinsing arrangement or rinsing station 101, to which the containers, namely bottles 130, are fed in the direction of travel as indicated by the arrow 131, by a first conveyer arrangement 103, which can be a linear conveyor or a combination of a linear conveyor and a starwheel. According to at least one possible embodiment, the rinsing arrangement or rinsing station 101 could utilize or be adapted to utilize an inspection device 10 for inspecting rinsed containers.

Downstream of the rinsing arrangement or rinsing station 101, in the direction of travel as indicated by the arrow 131, the rinsed bottles 130 are transported to a beverage filling machine 105 by a second conveyer arrangement 104 that is formed, for example, by one or more starwheels that introduce bottles 130 into the beverage filling machine 105.

The beverage filling machine 105 shown is of a revolving or rotary design, with a rotor 105', which revolves around a central, vertical machine axis. The rotor 105' is designed to receive and hold the bottles 130 for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles 130 to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 1A, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 12.2. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle 130, the first product or the second product can be filled by means of an appropriate control of the filling product or fluid valves.

According to at least one possible embodiment, the beverage filling machine 105 could utilize or be adapted to utilize an inspection device 10 for inspecting rinsed containers before filling, or for inspecting filled containers.

Downstream of the beverage filling machine 105, in the direction of travel of the bottles 130, there can be a beverage bottle closing arrangement or closing station 106 which closes or caps the bottles 130. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles 130. In the embodiment shown, the labeling arrangement 108 is connected by a starwheel conveyer structure to three output conveyer arrangements: a first output conveyer arrangement 109, a second output conveyer arrangement 110, and a third output conveyer arrangement 111, all of which convey filled, closed, and labeled bottles 130 to different locations.

The first output conveyer arrangement 109, in the embodiment shown, is designed to convey bottles 130 that are filled with a first type of liquid beverage supplied by, for example, the supply reservoir 123. The second output conveyer arrangement 110, in the embodiment shown, is designed to convey bottles 130 that are filled with a second type of liquid beverage supplied by, for example, the supply reservoir 124. The third output conveyer arrangement 111, in the embodiment shown, is designed to convey incorrectly labeled bottles 130. To further explain, the labeling arrangement 108 can comprise at least one beverage bottle inspection or monitoring device that inspects or monitors the location of labels on the bottles 130 to determine if the labels have been correctly placed or aligned on the bottles 130. The third output conveyer arrangement 111 removes any bottles 130 which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

Figure 3:
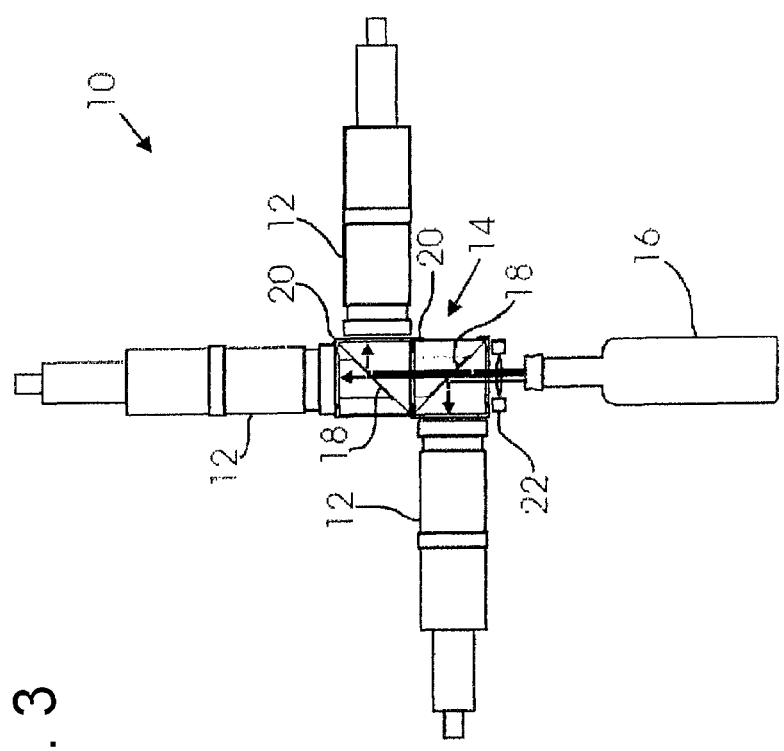
FIG. 3 shows a first possible embodiment of an inspection device.

In FIG. 3, by way of example, a first embodiment of an inspection device 10 is shown, in which various cameras 12, there being three in the example shown, inspect a container 16 to be inspected by means of optical paths which run through an optical channel 14. The container 16, in at least one embodiment, may be a bottle or similar container, such as, for example, a glass or plastic bottle for holding beverages or other liquids or products to be contained in a bottle.

Figure 3A:
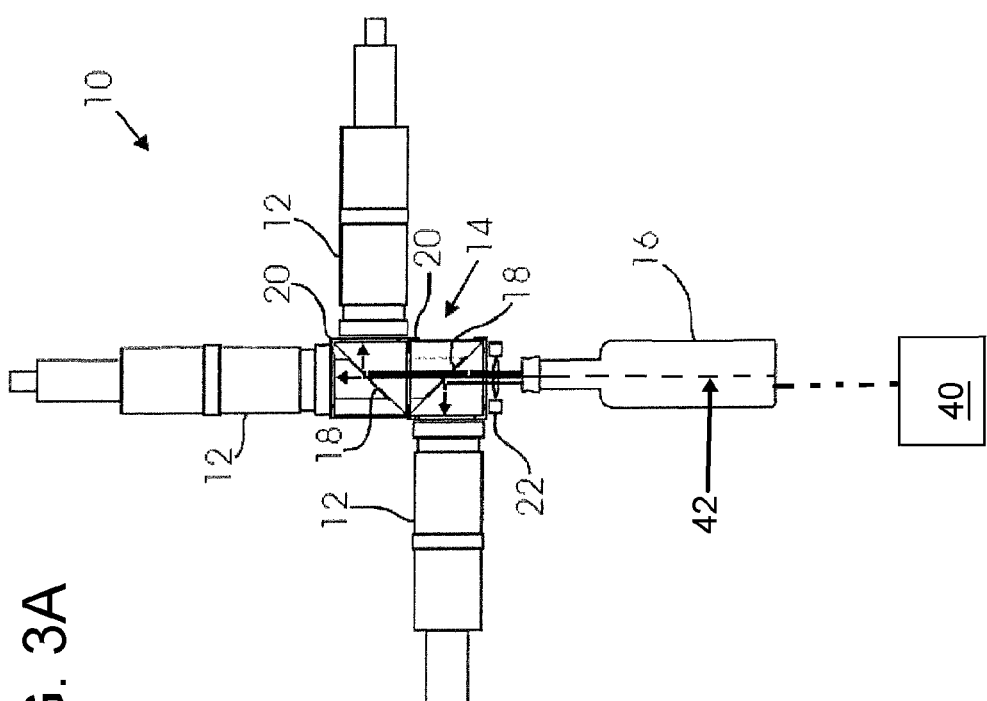
FIG. 3A shows a possible embodiment of the inspection device according to FIG. 3.

A lighting device 40 is positioned so as to illuminate or direct light through a portion or portions of a container 16 made of transparent or translucent material, for example glass or plastic. For example, as shown in FIG. 3A, the lighting device may be positioned underneath the container. Light thus shines through the container 16 and is thereby observed through the mouth region of the container 16. FIG. 3A also shows that the container 16 may have a vertical or rotational axis 42.

To this end, the inspection device 10 has inlet optics, that is, a lens arrangement or lens system 22. Optical paths (shown by lines with arrows proceeding from the mouth of the container 16 in FIG. 3) run between the cameras 12 and the container 16 through the optical channel 14 and the lens arrangement 22.

Within the optical channel 14 is disposed at least one optical element 18 with partially transparent and partially reflective optical properties. In the embodiment shown in FIG. 3, there are two optical elements 18 located in the optical channel 14, which optical elements 18 function as beam splitters. In this way, the image of the container 16 is split into three separate optical paths to the cameras 12, so that each camera 12 can inspect, in each case, an allocated region of the container 16.

Moreover, the optical channel 14 is formed in the illustrated example by two cubic channel elements 20. In the example shown, the cubic channel elements 20 are arranged directly over each other along a longitudinal axis 42 of the container, and each have inserts 26 on which the optical elements 18, such as beam splitters, are arranged.

FIG. 1 shows in a perspective view how an optical channel 14 can be made in a modular manner from cubic channel elements 20. As shown there, each channel element 20 is designed as a cubic hollow body with a single-piece wall or frame or enclosure, which forms four lateral areas or walls or sides. The wall or frame or enclosure encloses an internal region, which has a substantially rectangular cross-section (i.e. with the exception of the rounded corners). In the illustrated example, the wall or frame or enclosure of the channel elements 20 is made of an aluminum cast material, though other suitable materials could be used.

Each channel element 20 is here structured rotationally symmetrically with four identical lateral areas, in which, in each case, one central opening 24 is provided. The openings 24 are used for the optical paths to pass through. They are in each case arranged aligned in pairs.

On the two remaining lateral areas, the channel elements 20 are open so that, as shown schematically in FIG. 1, an insert 26 can be pushed into the interior of the channel elements 20. On these lateral areas, the channel elements 20 can be closed by covers (not shown).

The insert 26 has appropriate dimensions so that it is guided when pushed into the channel elements 20, and thus is precisely positioned or in a desired position. The insert 26 has a base plate 28 and, in the possible embodiment shown, has a holding body 30 approximately triangular in cross-section, in which two holes or openings 32 are formed at right angles to each other. On the holding body 30, in addition a bracket or holder 38 is made for an optical element 18, such as a flat mirror or a beam-splitting optical element.

The insert 26 can be pushed in the interior of the channel elements 20 in four positions turned in each case ninety degrees relative to each other. In each position, the base plate 28 is guided on the wall and thus precisely or desirably positioned, wherein the outer contour of said base plate, being a rectangle or square with rounded corners, fits precisely or desirably in the interior region of each channel element 20. By means of covers (not illustrated) arranged on both sides of the channel element 20, the insert 26 is fixed in its position, wherein it can, for example, be screwed to the mounting holes illustrated in FIG. 1 with a cover.

Overall, in the arrangement of the channel elements 20 with respect to each other, and in the arrangement of the insert 26 inside a channel element 20, a tolerance of 0.1-0.2 millimeters can be maintained so that despite ease of handling, a very precise optical structure can be achieved.

In the arrangement of the insert 26 inside the channel element 20, the holes 32 essentially ensure or promote the optical passage between opposite openings 24 in the sides of the channel elements 20. In the example of an embodiment shown, the bracket 38 for the mirror or beam-splitting optical element 18 is thus arranged at forty-five degrees so that by reflection on the element an optical path is formed between the openings 24 in adjacent lateral areas, and the optical path is thus diverted by ninety degrees. In addition, as shown in FIG. 1, the flat optical element 18 is inserted in the corresponding bracket 38 on the holding body 30.

In alternative embodiments, the holding body 30 can have a different cross-sectional shape, for example a triangular shape with a different angle, so that instead of the possible right-angle deviation by means of the mirror/beam-splitting element of forty-five degrees, a deviation of other angles is also possible, and in one possible embodiment a trapezium shape, for example with two reflection areas at forty-five degrees, with which a splitting of the optical path is possible at for example ninety degrees in each case in two different directions.

To form the optical channel 14, the channel elements 20 are secured to each other. Mounting holes 36 are used for this, being provided in each channel element 20, in each case on four lateral areas with an identical drill pattern. By screwing on the mounting holes 36, the cameras 12 (not shown in FIG. 1) can also be secured on the optical channel 14.

Various optical channels can easily be built to a modular design from the channel elements 20. Likewise, an existing optical channel can be converted.

Figure 4:
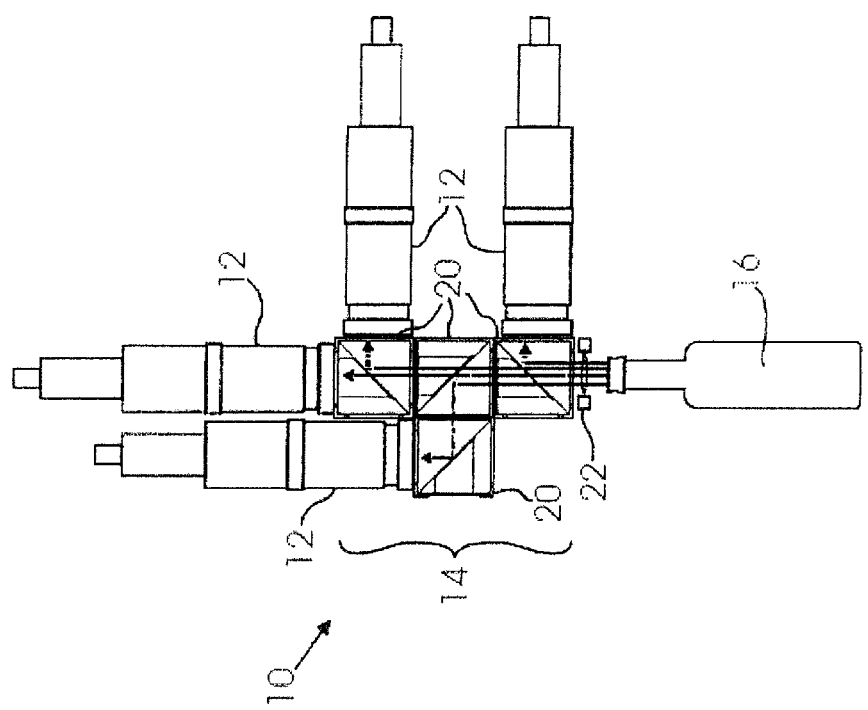
FIG. 4 shows a second possible embodiment of the inspection device.

For example, FIG. 4 shows a second embodiment of an inspection device 10, in this example with four cameras 12. Here, the optical channel 14 is built from four channel elements 20.

As the person skilled in the art can easily deduce, a multiplicity of different optical channels for many applications can be made with the cubic channel elements 20 and optical elements on the inserts 26. Here, the beam path length does not have to be measured individually for each system built in a modular manner from the channel elements 20, but in each case is a whole-number multiple of the edge length of the cubic channel elements 20, wherein the beam path length is overall independent of whether the possible optical path is guided straight through the channel elements or is reflected on a mirror or beam-splitting optical element 18. Accordingly adapted lenses on the lens arrangement 22 can be provided, to essentially guarantee or promote a suitable depiction of the relevant region for the allocated camera 12 with respect to the beam path length, which can be determined based on the edge length of the cubic channel elements 20.

Moreover, it should be understood that variations from the illustrated examples of embodiments are possible. For example, even inside the channel elements 20, brackets for optical elements can be provided in various positions so as to place the optical elements in different positions and/or orientations. Also, the present application is not restricted to the arrangements of channel elements selected in the illustrated examples, on one level; instead the channel elements can also be arranged one after the other on multiple levels.

Figure 5:
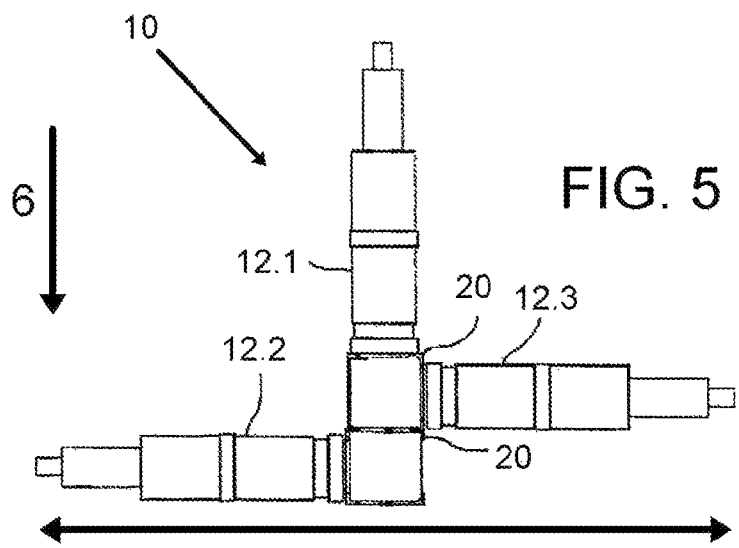
FIGS. 5, 5A, and 5B show various possible configurations of the inspection device according to at least one possible embodiment.
Figure 5A:
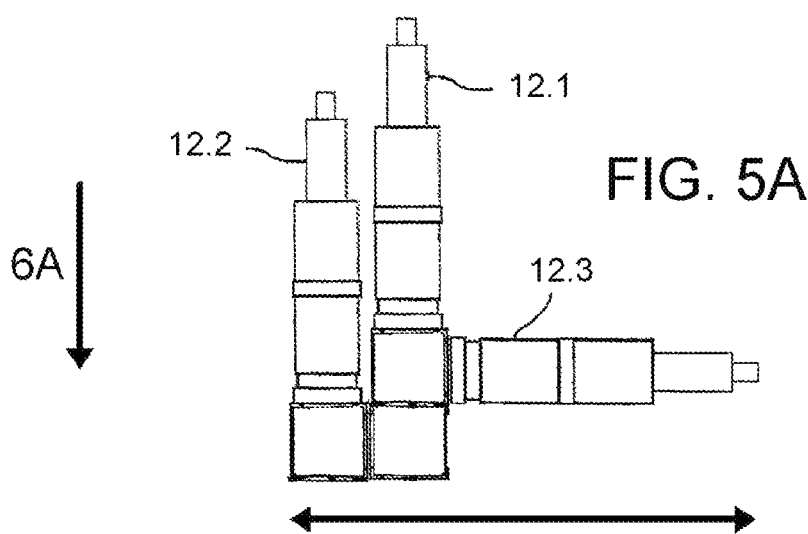
Figure 5B:
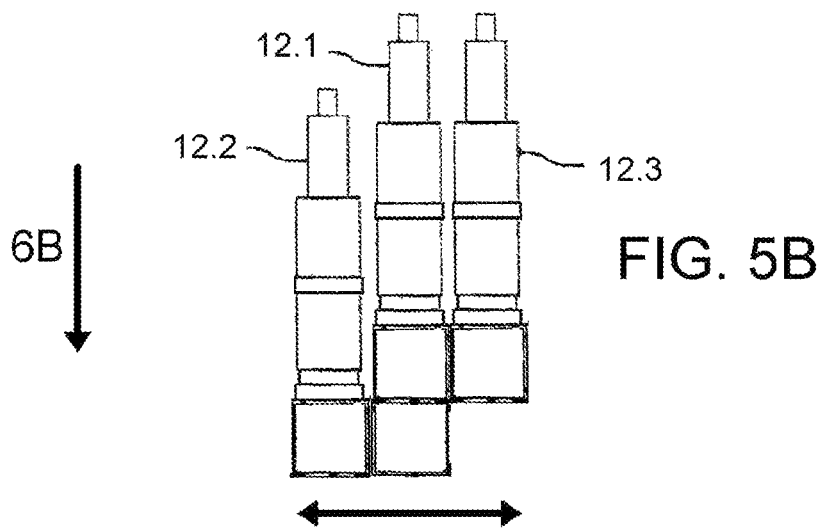
Figure 6:
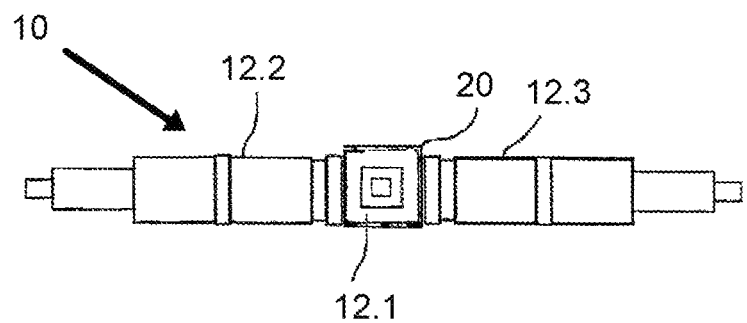
FIGS. 6, 6A, and 6B show alternative views of the configurations shown in FIGS. 5, 5A, and 5B.
Figure 6A:
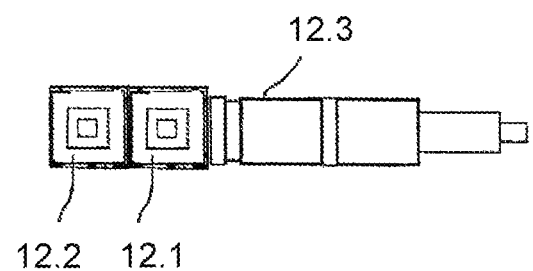
Figure 6B:
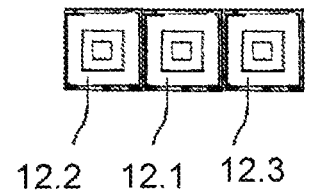

FIGS. 5, 5A, and 5B show various possible configurations of an inspection device 10 according to at least one possible embodiment. In each of these configurations, three cameras 12.1, 12.2, 12.3—or other imaging devices or a combination thereof—are utilized. In FIG. 5, the uppermost camera 12.1 is vertically oriented, whereas the two side cameras 12.2, 12.3 project out perpendicular or essentially perpendicular to the uppermost camera 12.1. Two channel elements 20 are utilized to direct the light beams accordingly. In contrast, in FIG. 5A, the left side camera 12.2 is oriented vertically so as to run parallel or essentially parallel to the uppermost camera 12.1. An additional channel element 20 is utilized in order to direct the light beam into the left side camera 12.2. Finally, FIG. 5B shows an embodiment in which all three cameras 12.1, 12.2, 12.3 are oriented vertically or essentially vertically. In this embodiment, four channel elements 20 are utilized. FIG. 6 shows a top view of the embodiment shown in FIG. 5 in the direction of arrow 6 in FIG. 5, FIG. 6A shows a top view of the embodiment shown in FIG. 5A in the direction of arrow 6A in FIG. 5A, and FIG. 6B shows a top view of the embodiment shown in FIG. 5B in the direction of arrow 6B in FIG. 5B.

As can be easily seen in FIGS. 5-5B and 6-6B, the design of the channel elements 20 allows for multiple configurations. By orienting the left side camera 12.2 vertically, as shown in FIG. 5A, the overall width (represented by the lines with the double arrows) of the inspection device 10 shown in FIG. 5 can be reduced by approximately one third or about 33 percent. By orienting both side cameras 12.2, 12.3 vertically, as shown in FIG. 5B, the overall width of the inspection device 10 shown in FIG. 5 can be reduced by approximately two thirds or about 66 percent. It should be noted that these calculations are based on the embodiments shown in the figures. If the cameras used are even longer than the cameras depicted in the figures, the space savings could be even greater, such as possibly 40 to 75 percent, which would represent a tremendous reduction in overall width of the inspection device 10. Thus, the different possible configurations of the cameras 12.1-12.3 permitted by the channel elements 20 could yield a space savings, at least along the width of the inspection device 10, of from about 33 percent to about 75 percent, plus or minus five percent. This range includes all whole number percent values, such as 35 percent, 36 percent, 37 percent, etc., as well as tenths of a percent, such as 35.1 percent, 35.2 percent, 35.3 percent, etc.

The channel elements 20 therefore advantageously allow the inspection device 10 to be configured in accordance with space requirements of a container handling machine in which the inspection device 10 is to be installed. Such versatility would be especially advantageous when the inspection device 10 is to be installed in an existing container handling machine, either at the time of manufacture/installation of the container handling machine, or after manufacture/installation in a retrofitting scenario. Depending on the design of the container handling machine and the space limitations relating thereto, the inspection device 10 could be configured in a variety of configurations in order to fit into the available space without requiring modification of the existing container handling machine.

This design and versatility would provide an economic benefit in that the manufacturer could easily create a number of unique, specifically-configured, inspection devices 10 as needed for different installations. Additionally, the manufacturer could provide a customer with essentially an inspection device kit that includes a plurality of identical components, such as channel elements 20, cameras 12, and inserts 26. The customer could then customize the assembly of the various parts to create an inspection device 10 that best fits their container handling device(s). In addition, the manufacturer would achieve an economic advantage by only having to manufacture a number of duplicate parts, rather than having to manufacture each individual inspection device 10 in accordance with the needs of a specific, individual installation.

Figure 7:
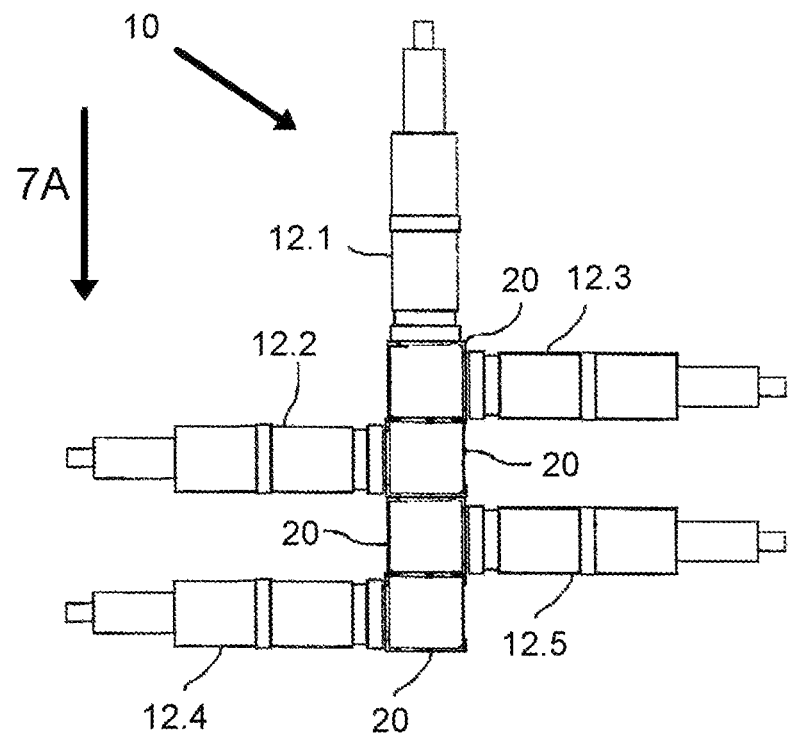
FIGS. 7 and 7A show two views of another possible configuration of the inspection device according to at least one possible embodiment.
Figure 7A:
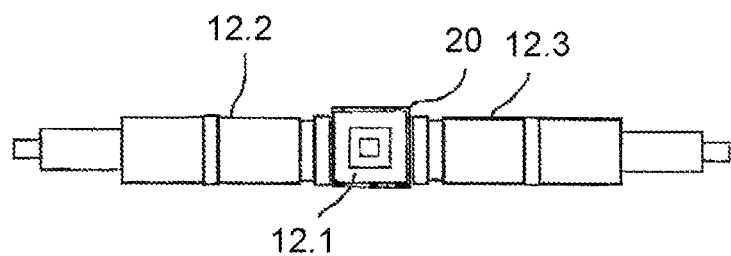
Figure 7B:
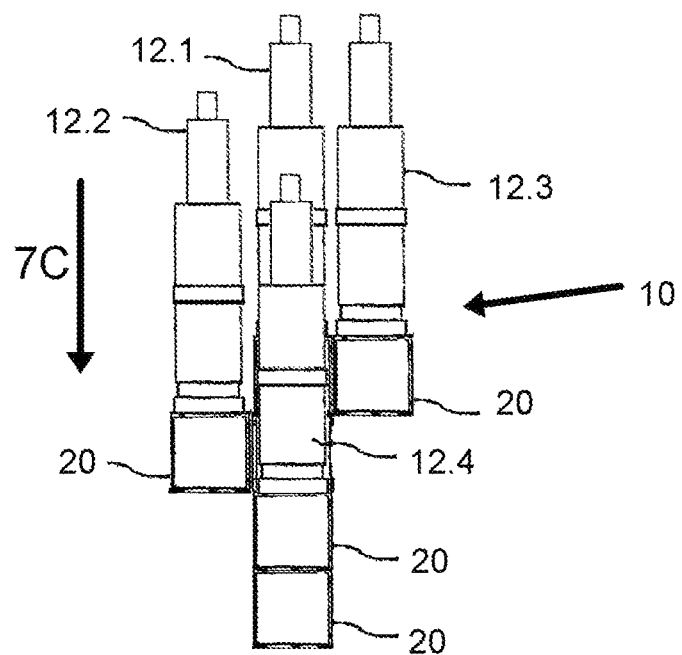
FIGS. 7B and 7C show two views of a different configuration of the inspection device shown in FIGS. 7 and 7A.
Figure 7C:
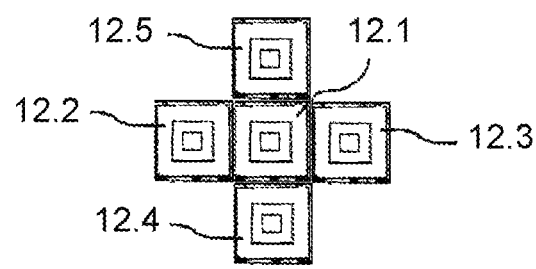

FIGS. 7 and 7A show two views of another possible configuration of the inspection device 10 according to at least one possible embodiment. In FIG. 7, the inspection device 10 utilizes five cameras 12.1-12.5, with two 12.2, 12.4 on the left side and two 12.3, 12.5 on the right side, and the fifth camera 12.1 being in the middle. FIG. 7A shows a top view of FIG. 7 as viewed along line 7A. In contrast, FIGS. 7B and 7C show two views of a different configuration of the inspection device 10 shown in FIGS. 7 and 7A. In FIG. 7B, all five cameras 12.1-12.5 are oriented vertically, with one camera 12.5 in the rear not visible. The top view in FIG. 7C (of FIG. 7B along line 7C) shows the arrangement of the cameras 12.1-12.5, with one central camera 12.1 and the four other cameras 12.2-12.5 oriented one on each side of the central camera 12.1. In the configuration in FIGS. 7B and 7C, the five cameras 12.1-12.5 are compacted into a much tighter space than the configuration shown in FIGS. 7 and 7A. Instead of the inspection device 10 taking up a rather large planar space, as in FIGS. 7 and 7A, the inspection device 10, according to FIGS. 7B and 7C, takes up a much more compact rectangular space.

Figure 8:
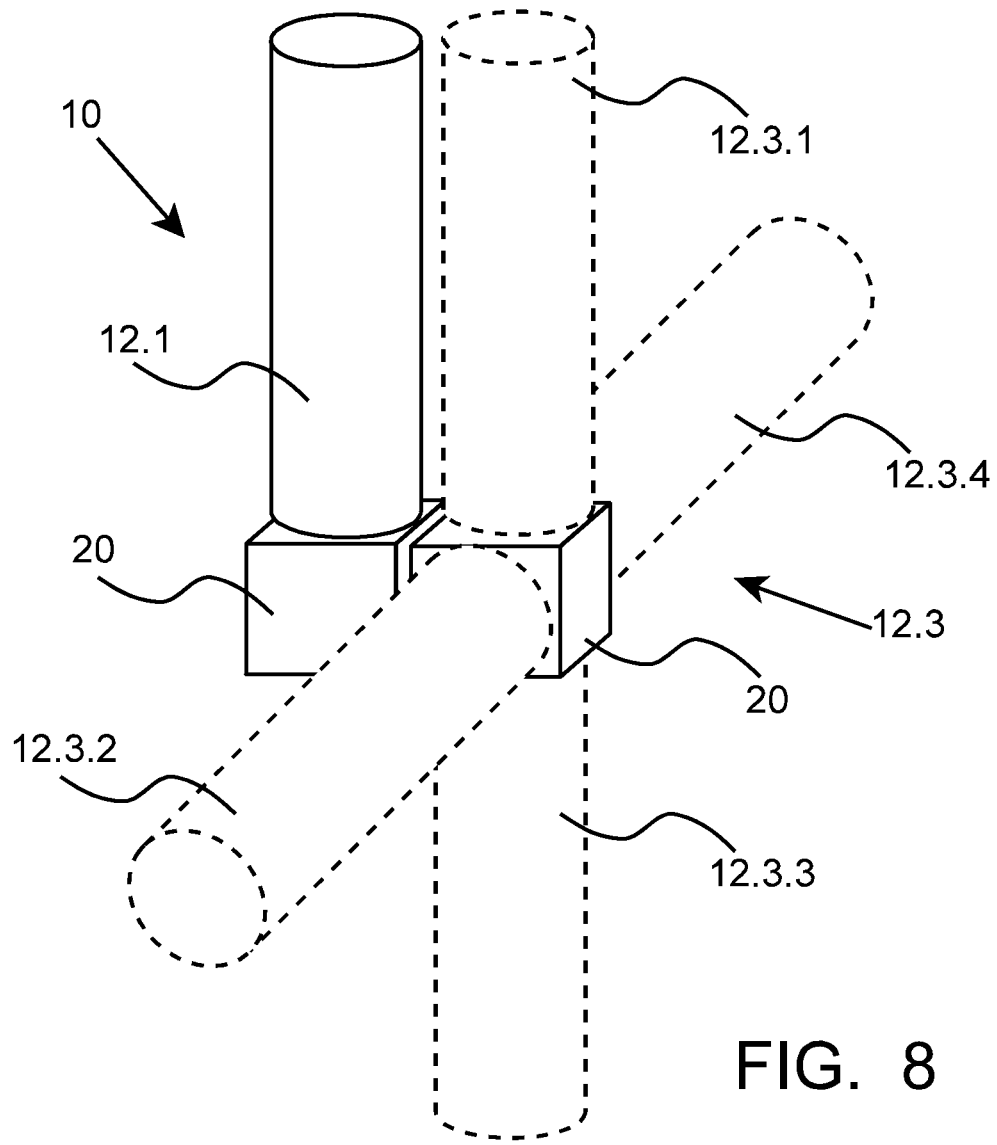
FIG. 8 shows a schematic, perspective view that represents different possible configurations of at least a portion of an inspection device according to at least one possible embodiment.

As discussed above and shown in the figures, many different configurations of various sizes and shapes are possible when utilizing the channel elements 20 according to at least one embodiment. In that regard, FIG. 8 shows a schematic, perspective view that represents different possible configurations of at least a portion of an inspection device 10 according to at least one possible embodiment. The two cubic or rectangular shapes represent the channel elements 20, and the cylindrical shapes represent the cameras 12.1 and 12.3. As can be seen in FIG. 8, the two cameras 12.1, 12.3 can be oriented four different ways with respect to one another, with the possible orientations (12.3.1, 12.3.2, 12.3.3, 12.3.4) shown by the cylinder in dotted lines. In addition, the camera 12.3 in dotted lines is positioned on only one side of the channel element 20 connected to the camera 12.1 in solid lines. By changing the position of the channel elements 20, twelve more configurations are possible, for a total of sixteen possible configurations. Further, if the two cameras 12.1, 12.3 share a single channel element 20, four more configurations are possible, bringing the total to twenty possible configurations using just two cameras 12.1, 12.3 and one or two channel elements 20. With every additional camera and channel element, the possible configurations increase substantially so that a very large number of configurations are possible. Again, this provides tremendous flexibility to create whatever configuration best suits a particular container handling machine and the related spatial requirements, while still achieving a desired inspection of the containers. Again, it should be understood that the embodiments and/or configurations shown in the figures are provided for exemplary purposes to show possible embodiments and/or configurations, and thus should not be construed as limiting the claims.

The following patents, patent applications, patent publications, and other patents documents are incorporated as if set forth in their entirety herein, except for the exceptions indicated herein: DE 10 2008 029 661 A1, having the German title "Redundante Inspektion", published on Dec. 31, 2009.

The present application relates to an inspection device 10 for inspecting containers 16. A first optical path runs through an optical channel 14 between a first camera and the container, and a second optical path runs through an optical channel between a second camera and the container. In order to be able to flexibly design the optical channel for different purposes, the channel has at least one identical or substantially identical channel element 20. Openings are provided on the channel elements, through which the optical paths run. On at least one of the channel elements, a receptacle is provided for a beam-splitting optical element 18, at which the first optical path is separated from the second optical path.

One feature or aspect of an embodiment is believed at the time of the filing of this patent application to possibly reside broadly in an inspection device for inspecting containers, comprising at least two cameras 12 for the optical inspection of at least one region of a container 16, and at least one optical channel 14, through which at least one optical path runs between a first camera 12 and the container 16, and a second optical path runs between a second camera 12 and the container 16, wherein the optical channel 14 has at least two identical or substantially identical channel elements 20 which in each case have openings 24 through which the optical paths run, and wherein at least one of the channel elements 20 has a holder 38 for a beam-splitting optical element 18 on which the first optical path is separated from the second optical path.

Another feature or aspect of an embodiment is believed at the time of the filing of this patent application to possibly reside broadly in the inspection device, in which the channel elements 20 are each designed as hollow elements in which a wall encloses an interior space.

Yet another feature or aspect of an embodiment is believed at the time of the filing of this patent application to possibly reside broadly in the inspection device, in which the channel elements 20 are in each case of a rectangular design, wherein at least three openings 24 are made in lateral areas of the cuboid, through which an optical path can run.

Still another feature or aspect of an embodiment is believed at the time of the filing of this patent application to possibly reside broadly in the inspection device, in which the channel elements 20 have a rotationally symmetrical structure.

A further feature or aspect of an embodiment is believed at the time of the filing of this patent application to possibly reside broadly in the inspection device, in which the channel elements 20 are designed as cubes.

Another feature or aspect of an embodiment is believed at the time of the filing of this patent application to possibly reside broadly in the inspection device, in which the channel elements 20 each have at least three openings 24, through which an optical path can run, of which at least a first and a second opening 24 are arranged in alignment, and a third opening 24 is arranged at an angle to them, and at least one bracket 38 for a beam-splitting optical element 18 or mirror element is provided so that an optical path runs from the first opening 24 by means of a reflection on the beam-splitting optical element 18 or mirror element to the third opening 24.

Yet another feature or aspect of an embodiment is believed at the time of the filing of this patent application to possibly reside broadly in the inspection device, in which at least one insert 26 is provided as a holder in a channel element 20, wherein the insert 26 has a bracket 38 for at least one optical element.

Still another feature or aspect of an embodiment is believed at the time of the filing of this patent application to possibly reside broadly in the inspection device, in which the insert 26 can be pushed along a guide into a channel element 20.

A further feature or aspect of an embodiment is believed at the time of the filing of this patent application to possibly reside broadly in the inspection device, in which the insert 26 has at least one opening 32 through which an optical path can pass.

Another feature or aspect of an embodiment is believed at the time of the filing of this patent application to possibly reside broadly in the inspection device, in which the insert 26 has two openings 32 through which optical paths can pass, wherein the openings 32 are made as drilled holes which form an angle to each other.

Yet another feature or aspect of an embodiment is believed at the time of the filing of this patent application to possibly reside broadly in the inspection device, in which the channel elements 20 in each case have lateral areas with an identical arrangement of a number of mounting holes 36.

Still another feature or aspect of an embodiment is believed at the time of the filing of this patent application to possibly reside broadly in the inspection device, in which at least one lens element is arranged in the optical path between the optical channel 14 and the container 16.

One feature or aspect of an embodiment is believed at the time of the filing of this patent application to possibly reside broadly in a channel element for use in an inspection device according to the present application.

One feature or aspect of an embodiment is believed at the time of the filing of this patent application to possibly reside broadly in a beverage bottle handling device in a beverage bottling plant for filling bottles with a liquid beverage, said beverage bottle handling device comprising: a beverage bottle conveyor arrangement configured to convey beverage bottles; at least one beverage bottle treatment device; said at least one beverage bottle treatment device comprising one of: a beverage bottle rinsing device configured to rinse empty beverage bottles; and a beverage bottle filling device configured to fill empty beverage bottles with a liquid beverage; said beverage bottle conveyor arrangement being configured to convey beverage bottles to and away from said at least one beverage bottle treatment device; a beverage bottle inspection device comprising at least two beverage bottle detection devices and at least two guide structures;

said at least two beverage bottle detection devices being configured to detect at least one portion of a beverage bottle; said at least two guide structures being configured to permit said at least two beverage bottle detection devices to detect the at least one portion of the beverage bottle; said guide structures comprising a first guide structure and a second guide structure; a holding structure being disposed in said first guide structure; and a guide element being held by said holding structure.

Another feature or aspect of an embodiment is believed at the time of the filing of this patent application to possibly reside broadly in the beverage bottle handling device, for use in a beverage bottling plant for filling bottles with a liquid beverage, wherein: each of said at least two guide structures is a hollow element, which hollow element comprises a wall or frame that encloses an interior space; each of said at least two guide structures is in the shape of a rectangular box or cube comprising at least four lateral wall portions; each of said at least two guide structures comprises a rotationally symmetrical structure; each of said at least two guide structures comprises at least three openings, one opening each in a corresponding one of said lateral wall portions; said at least three openings comprise a first opening, a second opening, and a third opening, wherein said first opening and said second opening are aligned with one another, and said third opening is disposed at an angle with respect to each of said first opening and said second opening; said holding structure comprises an insert configured to be inserted into the interior space of one of said guide structures; said holding structure comprises a bracket configured to hold said guide element; each of said guide structures comprises an insert guide configured to guide said holding structure during insertion; said holding structure comprises at least one opening therein, or at least two openings therein disposed at an angle with respect to one another; and each of said lateral wall portions comprises an identical arrangement of a plurality of mounting holes.

Yet another feature or aspect of an embodiment is believed at the time of the filing of this patent application to possibly reside broadly in a container inspection device to inspect containers, such as bottles or similar containers in a container filling plant, said container inspection device comprising: a sensor arrangement comprising at least two sensors being configured to sense characteristics of at least one region of a container; said at least two sensors comprising a first sensor and a second sensor; a guide arrangement being configured to guide characteristic information of the at least one region of the container along a first guide path to said first sensor, and along a separate, second guide path to said second sensor; said guide arrangement comprising at least two essentially identical guide structures; each of said guide structures comprising openings through which said guide paths travel; said guide structures comprising a first guide structure and a second guide structure; a holding structure being disposed in said first guide structure; a guide element being configured to guide characteristic information of at least one region of a container to both said first guide path and said second guide path; and said holding structure being configured and disposed to hold said guide element.

Still another feature or aspect of an embodiment is believed at the time of the filing of this patent application to possibly reside broadly in the container inspection device, wherein: said first sensor comprises a first camera, and said second sensor comprises a second camera; and said guide element is configured to divide a light beam traveling from a container into two beams, such that a first beam travels along said first path to said first camera, and said second beam travels along said second path to said second camera.

A further feature or aspect of an embodiment is believed at the time of the filing of this patent application to possibly reside broadly in the container inspection device, wherein each of said at least two guide structures is a hollow element, which hollow element comprises a frame that encloses an interior space.

Another feature or aspect of an embodiment is believed at the time of the filing of this patent application to possibly reside broadly in the container inspection device, wherein one of (A) and (B): (A) each of said at least two guide structures is in the shape of a rectangular cuboid comprising four lateral wall portions; and at least three of said lateral wall portions have openings therein through which a guide path can travel; and (B) each of said at least two guide structures is in the shape of a cube comprising four lateral wall portions; and at least three of said lateral wall portions have openings therein through which a guide path can travel.

Yet another feature or aspect of an embodiment is believed at the time of the filing of this patent application to possibly reside broadly in the container inspection device, wherein each of said at least two guide structures comprises a rotationally symmetrical structure, such that each of said four lateral wall portions has an opening therein.

Still another feature or aspect of an embodiment is believed at the time of the filing of this patent application to possibly reside broadly in the container inspection device, wherein: said openings comprise a first opening, a second opening, and a third opening, wherein said first opening and said second opening are aligned with one another, and said third opening is disposed at an angle with respect to each of said first opening and said second opening; said holding structure comprises an insert configured to be inserted into the interior space of one of said guide structures; and said holding structure comprises a bracket configured to hold said guide element.

A further feature or aspect of an embodiment is believed at the time of the filing of this patent application to possibly reside broadly in the container inspection device, wherein each of said guide structures comprises an insert guide configured to guide said holding structure during insertion.

Another feature or aspect of an embodiment is believed at the time of the filing of this patent application to possibly reside broadly in the container inspection device, wherein: said holding structure comprises at least one opening therein, or at least two openings therein disposed at an angle with respect to one another; and each of said lateral wall portions comprises an identical arrangement of a plurality of mounting holes.

Yet another feature or aspect of an embodiment is believed at the time of the filing of this patent application to possibly reside broadly in the container inspection device, wherein the container inspection device further comprises a lens element disposed at an end of the inspection device such that, upon a container being moved adjacent said inspection device, said lens element is between said guide arrangement and the container.

Still another feature or aspect of an embodiment is believed at the time of the filing of this patent application to possibly reside broadly in a container inspection device to inspect containers, such as bottles or similar containers in a container filling plant, said container inspection device comprising: a guide arrangement being configured to guide characteristic information of at least one region of a container along a first guide path to a first sensor, and along a separate, second guide path to a second sensor; said guide arrangement comprising at least two essentially identical guide structures; each of said guide structures comprising openings through which said guide paths travel; said guide structures comprising a first guide structure and a second guide structure; a holding structure being disposed in said first guide structure; a guide element being configured to guide characteristic information of at least one region of a container to both said first guide path and said second guide path; and said holding structure being configured and disposed to hold said guide element.

A further feature or aspect of an embodiment is believed at the time of the filing of this patent application to possibly reside broadly in the container inspection device, wherein said guide element is configured to divide a light beam traveling from a container into two beams, such that a first beam travels along the first path, and said second beam travels along the second path.

One feature or aspect of an embodiment is believed at the time of the filing of this patent application to possibly reside broadly in the container inspection device, wherein: each of said at least two guide structures is a hollow element, which hollow element comprises a frame that encloses an interior space; one of (A) and (B): (A) each of said at least two guide structures is in the shape of a rectangular cuboid comprising four lateral wall portions; and at least three of said lateral wall portions have openings therein through which a guide path can travel; and (B) each of said at least two guide structures is in the shape of a cube comprising four lateral wall portions; and at least three of said lateral wall portions have openings therein through which a guide path can travel.

Another feature or aspect of an embodiment is believed at the time of the filing of this patent application to possibly reside broadly in the container inspection device, wherein: each of said at least two guide structures comprises a rotationally symmetrical structure, such that each of said four lateral wall portions has an opening therein; said openings comprise a first opening, a second opening, and a third opening, wherein said first opening and said second opening are aligned with one another, and said third opening is disposed at an angle with respect to each of said first opening and said second opening; said holding structure comprises an insert configured to be inserted into the interior space of one of said guide structures; and said holding structure comprises a bracket configured to hold said guide element.

Yet another feature or aspect of an embodiment is believed at the time of the filing of this patent application to possibly reside broadly in the container inspection device, wherein: each of said guide structures comprises an insert guide configured to guide said holding structure during insertion; said holding structure comprises at least one opening therein, or at least two openings therein disposed at an angle with respect to one another; and each of said lateral wall portions comprises an identical arrangement of a plurality of mounting holes.

Still another feature or aspect of an embodiment is believed at the time of the filing of this patent application to possibly reside broadly in the container inspection device, wherein: each of said guide structures is in the shape of a rectangular cuboid or a cube, and comprises at least four essentially identical side walls that surround a hollow interior space; and said guide structures are configured to be detachably connected to one another at any of said side walls to permit a plurality of configurations of the guide arrangement in accordance with a desired inspection procedure and spatial restrictions of a container handling machine in which the guide arrangement is to be installed.

A further feature or aspect of an embodiment is believed at the time of the filing of this patent application to possibly reside broadly in the container inspection device, wherein: said holding structure is in the form of an insert configured to be inserted into the hollow interior space in one of said guide structures; said holding structure comprises an angled side at which said guide element is held, which angled side, upon insertion of said holding structure into its guide structure, is disposed at an angle with respect to at least one said side walls; and said holding structure essentially conforms to the hollow interior space, and is configured to be rotated about at least one axis, to permit a plurality of orientations of said angled side in its guide structure, to thereby permit directing of light beams along a plurality of guide paths in accordance with a desired inspection procedure and spatial restrictions of a container handling machine in which the guide arrangement is to be installed.

Another feature or aspect of an embodiment is believed at the time of the filing of this patent application to possibly reside broadly in the container inspection device, wherein: said at least two essentially identical guide structures comprise a plurality of essentially identical, interchangeable, guide structures; each of said guide structures is in the shape of a rectangular cuboid or a cube, and comprises at least four essentially identical side walls that surround a hollow interior space; said holding structure comprises a plurality of holding structures, and said guide element comprises a plurality of guide elements; and said guide structures are configured to be detachably connected to one another at any of said side walls to permit a plurality of configurations of the guide arrangement in accordance with a desired inspection procedure and spatial restrictions of a container handling machine in which the guide arrangement is to be installed.

Yet another feature or aspect of an embodiment is believed at the time of the filing of this patent application to possibly reside broadly in a method of inspecting containers using a container inspection device, said method comprising the steps of: selecting a first guide structure and a second guide structure from said plurality of essentially identical guide structures; selecting a first holding structure and a second holding structure from said plurality of holding structures; selecting a first guide element and a second guide element from said plurality of guide elements, and then placing said first guide element in said first holding structure, and said second guide element in said second holding structure; placing said first holding structure, and thus said first guide element, in said first guide structure in a desired orientation, and placing said second holding structure, and thus said second guide element, in said second guide structure in a desired orientation; arranging said first guide structure with respect to said second guide structure in the container inspection arrangement to define at least two guide paths traveling through said guide elements, said holding structures, and said guide structures, and connecting said first and second guide structures together; and guiding characteristic information of at least one region of a container along both said first guide path and said second guide path in an inspection procedure.

The components disclosed in the patents, patent applications, patent publications, and other documents disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, patent applications, patent publications, and other documents either incorporated by reference or not incorporated by reference.

All of the patents, patent applications, patent publications, and other documents, except for the exceptions indicated herein, which were cited in the German Office Action dated Nov. 6, 2013, and/or cited elsewhere, as well as the German Office Action document itself, are hereby incorporated by reference as if set forth in their entirety herein except for the exceptions indicated herein, as follows: DE3611536 (A1), having the title "Device for automatically testing transparent objects, in particular glass bottles", published on Oct. 15, 1987; DE102006034432 (A1), having the German title "Inspektionsvorrichtung für Behältnisse", published on Jan. 31, 2008; and U.S. Pat. No. 6,172,748 (B1), having the title "Machine vision system and method for non-contact container inspection", published on Jan. 9, 2001.

All of the patents, patent applications, patent publications, and other documents, except for the exceptions indicated herein, which were cited in the International Search Report dated Jun. 16, 2014, and/or cited elsewhere, as well as the International Search Report document itself, are hereby incorporated by reference as if set forth in their entirety herein except for the exceptions indicated herein, as follows: GB2373556 (A), having the title "Modular optical construction system", published on Sep. 25, 2002; US2004264841 (A1), having the title "Adjusting carrier for setting optical elements", published on Dec. 30, 2004; and U.S. Pat. No. 5,490,011 (A), having the title "Modular enclosure assembly", published on Feb. 6, 1996.

The corresponding foreign and international patent publication applications, namely, Federal Republic of Germany Patent Application No. 10 2013 101 995.1, filed on Feb. 28, 2013, having inventors Carsten BUCHWALD and Wolfgang SCHORN, and DE-OS 10 2013 101 995.1 and DE-PS 10 2013 101 995.1, and International Application No. PCT/EP2014/000090, filed on Jan. 15, 2014, having WIPO Publication No. WO 2014/131484 and inventors Carsten BUCHWALD and Wolfgang SCHORN, are hereby incorporated by reference as if set forth in their entirety herein, except for the exceptions indicated herein, for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications, patent publications, and other documents, except for the exceptions indicated herein, are hereby incorporated by reference as if set forth in their entirety herein except for the exceptions indicated herein.

The purpose of incorporating the corresponding foreign equivalent patent application(s), that is, PCT/EP2014/000090 and German Patent Application 10 2013 101 995, is solely for the purposes of providing a basis of correction of any wording in the pages of the present application, which may have been mistranslated or misinterpreted by the translator, and to provide additional information relating to technical features of one or more embodiments, which information may not be completely disclosed in the wording in the pages of this application.

Statements made in the original foreign patent applications PCT/EP2014/000090 and DE 10 2013 101 995 from which this patent application claims priority which do not have to do with the correction of the translation in this patent application are not to be included in this patent application in the incorporation by reference.

Any statements about admissions of prior art in the original foreign patent applications PCT/EP2014/000090 and DE 10 2013 101 995 are not to be included in this patent application in the incorporation by reference, since the laws relating to prior art in non-U.S. Patent Offices and courts may be substantially different from the Patent Laws of the United States.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the embodiments therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, patent publications, and other documents, are not considered to be incorporated by reference herein for any of the patents, patent applications, patent publications, and other documents cited herein.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A container inspection device to inspect containers, comprising bottles or similar containers in a container filling plant, said container inspection device comprising:
   a sensor arrangement comprising at least two sensors being configured to sense characteristics of at least one region of a container;
   said at least two sensors comprising a first sensor and a second sensor;
   a guide arrangement being configured to guide characteristic information of the at least one region of the container along a first guide path to said first sensor, and along a separate, second guide path to said second sensor;
   said guide arrangement comprising at least two guide structures;
   each of said at least two guide structures comprising openings through which said guide paths travel;
   each of said at least two guide structures comprising a hollow frame that encloses an interior space;
   a holding structure being disposed in one of said at least two guide structures, which said holding structure comprises an insert configured to be removably inserted into the interior space of one of said at least two guide structures;
   a guide element being configured to guide characteristic information of at least one region of a container to both said first guide path and said second guide path; and
   said holding structure being configured and disposed to hold said guide element.

2. The container inspection device according to claim 1, wherein said holding structure comprises a bracket to hold said guide element.

3. The container inspection device according to claim 2, wherein said at least two guide structures are modular and are designed to be put together in at least two different configurations, each with different guide paths.

4. The container inspection device according to claim 2, wherein:
   said first sensor comprises a first camera, and said second sensor comprises a second camera; and said guide element is configured to divide a light beam traveling from a container into two beams, such that a first beam travels along said first path to said first camera, and said second beam travels along said second path to said second camera.

5. The container inspection device according to claim 4, wherein one of (A) and (B):
(A) each of said at least two guide structures is in the shape of a rectangular cuboid comprising four lateral wall portions; and
at least three of said lateral wall portions have openings therein through which a guide path can travel; and
(B) each of said at least two guide structures is in the shape of a cube comprising four lateral wall portions; and
at least three of said lateral wall portions have openings therein through which a guide path can travel.

6. The container inspection device according to claim 5, wherein each of said at least two guide structures comprises a rotationally symmetrical structure, such that each of said four lateral wall portions has an opening therein.

7. The container inspection device according to claim 6, wherein
said openings comprise a first opening, a second opening, and a third opening, wherein said first opening and said second opening are aligned with one another, and said third opening is disposed at an angle with respect to each of said first opening and said second opening.

8. The container inspection device according to claim 7, wherein each of said at least two guide structures comprises an insert guide configured to guide said holding structure during insertion.

9. The container inspection device according to claim 8, wherein:
said holding structure comprises at least one opening therein, or at least two openings therein disposed at an angle with respect to one another; and
each of said lateral wall portions comprises an identical arrangement of a plurality of mounting holes.

10. The container inspection device according to claim 9, wherein the container inspection device further comprises a lens element disposed at an end of the inspection device such that, upon a container being moved adjacent said inspection device, said lens element is between said guide arrangement and the container.

11. A container inspection device to inspect containers, such as bottles or similar containers in a container filling plant, said container inspection device comprising:
a guide arrangement being configured to guide characteristic information of at least one region of a container along a first guide path to a first sensor, and along a separate, second guide path to a second sensor;
said guide arrangement comprising at least two guide structures;
each of said at least two guide structures comprising openings through which said guide paths travel;
each of said at least two guide structures comprising a hollow frame that encloses an interior space;
a holding structure being disposed in one of said at least two guide structures, which said holding structure comprises an insert configured to be removably inserted into the interior space of one of said at least two guide structures;
a guide element being configured to guide characteristic information of at least one region of a container to both said first guide path and said second guide path; and
said holding structure being configured and disposed to hold said guide element.

12. The container inspection device according to claim 11, wherein said holding structure comprises a bracket to hold said guide element.

13. The container inspection device according to claim 12, wherein said at least two guide structures are modular and are designed to be put together in at least two different configurations, each with different guide paths.

14. The container inspection device according to claim 12, wherein said guide element is configured to divide a light beam traveling from a container into two beams, such that a first beam travels along the first path, and said second beam travels along the second path.

15. The container inspection device according to claim 14, wherein:
one of (A) and (B):
(A) each of said at least two guide structures is in the shape of a rectangular cuboid comprising four lateral wall portions; and
at least three of said lateral wall portions have openings therein through which a guide path can travel; and
(B) each of said at least two guide structures is in the shape of a cube comprising four lateral wall portions; and
at least three of said lateral wall portions have openings therein through which a guide path can travel.

16. The container inspection device according to claim 15, wherein:
each of said at least two guide structures comprises a rotationally symmetrical structure, such that each of said four lateral wall portions has an opening therein; and
said openings comprise a first opening, a second opening, and a third opening, wherein said first opening and said second opening are aligned with one another, and said third opening is disposed at an angle with respect to each of said first opening and said second opening.

17. The container inspection device according to claim 16, wherein:
each of said at least two guide structures comprises an insert guide configured to guide said holding structure during insertion;
said holding structure comprises at least one opening therein, or at least two openings therein disposed at an angle with respect to one another; and
each of said lateral wall portions comprises an identical arrangement of a plurality of mounting holes.

18. A beverage bottle handling device in a beverage bottling plant for filling bottles with a liquid beverage, said beverage bottle handling device comprising:
a beverage bottle conveyor arrangement configured to convey beverage bottles;
at least one beverage bottle treatment device;
said at least one beverage bottle treatment device comprising one of:
a beverage bottle rinsing device configured to rinse empty beverage bottles; and
a beverage bottle filling device configured to fill empty beverage bottles with a liquid beverage;
said beverage bottle conveyor arrangement being configured to convey beverage bottles to and away from said at least one beverage bottle treatment device;
a beverage bottle inspection device comprising at least two beverage bottle detection devices and at least two guide structures;

said at least two beverage bottle detection devices being configured to detect at least one portion of a beverage bottle;

said at least two guide structures being configured to permit said at least two beverage bottle detection devices to detect the at least one portion of the beverage bottle;

each of said at least two guide structures comprising a hollow frame that encloses an interior space;

a holding structure being disposed in one of said at least two guide structures, which said holding structure comprises an insert configured to be removably inserted into the interior space of one of said at least two guide structures; and a guide element being held by said holding structure.

19. The beverage bottle handling device according to claim 18, wherein said holding structure comprises a bracket to hold said guide element.

20. The beverage bottle handling device according to claim 19, wherein:

each of said at least two guide structures is in the shape of a rectangular box or cube comprising at least four lateral wall portions;

each of said at least two guide structures comprises a rotationally symmetrical structure;

each of said at least two guide structures comprises at least three openings, one opening each in a corresponding one of said lateral wall portions;

said at least three openings comprise a first opening, a second opening, and a third opening, wherein said first opening and said second opening are aligned with one another, and said third opening is disposed at an angle with respect to each of said first opening and said second opening;

each of said at least two guide structures comprises an insert guide configured to guide said holding structure during insertion;

said holding structure comprises at least one opening therein, or at least two openings therein disposed at an angle with respect to one another;

each of said lateral wall portions comprises an identical arrangement of a plurality of mounting holes; and said at least two guide structures are modular and are designed to be put together in at least two different configurations, each with different guide paths.

\* \* \* \* \*